US012390284B2

United States Patent
Govari et al.

(10) Patent No.: US 12,390,284 B2
(45) Date of Patent: Aug. 19, 2025

(54) MAGNETIC LOCATION SENSOR AND ULTRASOUND ARRAY ON PRINTED-CIRCUIT-BOARD (PCB) OF CATHETER AND CALIBRATION THEREOF

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 18/202,340

(22) Filed: May 26, 2023

(65) Prior Publication Data

US 2023/0301724 A1    Sep. 28, 2023

Related U.S. Application Data

(62) Division of application No. 17/483,065, filed on Sep. 23, 2021, now abandoned.

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/0833* (2013.01); *A61B 8/12* (2013.01); *A61B 8/4254* (2013.01);
(Continued)

(58) Field of Classification Search
CPC ......... A61B 34/20; A61B 8/12; A61B 8/4254; A61B 8/587; A61B 3024/2051
See application file for complete search history.

(56) References Cited

U.S. PATENT DOCUMENTS

| 5,391,199 A | 2/1995 | Ben-Haim |
| 6,239,724 B1 | 5/2001 | Doron et al. |

(Continued)

FOREIGN PATENT DOCUMENTS

| CN | 113397602 | 9/2021 |
| WO | WO9605768 | 2/1996 |
| WO | WO2020/026254 | 2/2020 |

OTHER PUBLICATIONS

Wildes, D. et al., "4D ICE: A 2D Array Transducer With Integrated ASIC in a 10-Fr Catheter for Real-Time 3D Intracardiac Echocardiography," in IEEE Transactions on Ultrasonics, Ferroelectrics, and Frequency Control, vol. 63, No. 12, pp. 2159-2173, Dec. 2016, doi: 0.1109/TUFFC.2016.2615602.
(Continued)

Primary Examiner — Ashley K Buran
Assistant Examiner — Tommy T Ly
(74) Attorney, Agent, or Firm — Smith, Gambrell & Russell LLP; Michael J. Riesen

(57) ABSTRACT

A medical probe includes a shaft and a distal-end assembly. The shaft is configured for insertion into an organ of a body. The distal-end assembly is fitted at a distal end of the shaft. The distal-end assembly includes (a) a substrate, (b) a two-dimensional (2D) ultrasound transducer array located on the substrate, and (c) a sensor, which is also located on the substrate, the sensor configured to output signals indicative of a position and an orientation of the 2D ultrasound transducer array inside the organ.

14 Claims, 3 Drawing Sheets

(51) Int. Cl.
*A61B 8/08* (2006.01)
*A61B 8/12* (2006.01)
*G01R 35/00* (2006.01)
*G01S 7/52* (2006.01)
*G01S 15/89* (2006.01)

(52) U.S. Cl.
CPC ............ *A61B 8/445* (2013.01); *A61B 8/4488* (2013.01); *A61B 8/587* (2013.01); *G01R 35/005* (2013.01); *G01S 7/5205* (2013.01); *G01S 15/8906* (2013.01); *A61B 2034/2046* (2016.02); *A61B 2034/2051* (2016.02)

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 7,996,057 B2 | 8/2011 | Govari et al. |
| 9,468,422 B2 | 10/2016 | Hyun et al. |
| 9,980,786 B2 | 5/2018 | Saul et al. |
| 10,537,306 B2 | 1/2020 | Schaer et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0254458 A1* | 12/2004 | Govari ................... A61B 5/062 600/437 |
| 2007/0078345 A1 | 4/2007 | Mo et al. |
| 2007/0106156 A1* | 5/2007 | Altmann ................ A61B 8/4254 600/437 |
| 2009/0177089 A1 | 7/2009 | Govari et al. |
| 2017/0049357 A1 | 2/2017 | Eichler et al. |
| 2017/0119348 A1* | 5/2017 | Degertekin ......... G01S 15/8925 |
| 2017/0258439 A1 | 9/2017 | Jasperson et al. |
| 2018/0160936 A1* | 6/2018 | Govari ................... H05K 1/028 |
| 2018/0172420 A1 | 6/2018 | Hein et al. |
| 2018/0192991 A1 | 7/2018 | Kanade et al. |
| 2018/0220926 A1 | 8/2018 | Kelly et al. |
| 2018/0228392 A1 | 8/2018 | Govari et al. |
| 2018/0289356 A1* | 10/2018 | Buesseler ......... A61M 25/0136 |
| 2019/0380687 A1* | 12/2019 | Peled ...................... A61B 8/12 |
| 2020/0061340 A1 | 2/2020 | Mixter et al. |
| 2022/0071592 A1* | 3/2022 | Yamamoto ........... A61B 8/4488 |
| 2023/0091133 A1 | 3/2023 | Govari et al. |
| 2024/0164751 A1* | 5/2024 | Lupotti ................ A61B 8/0891 |

OTHER PUBLICATIONS

U.S. Appl. No. 17/357,231, filed Jun. 24, 2021.
Extended European Search Report dated Feb. 15, 2023 from corresponding EP No. 22197016.3-1126.

* cited by examiner

MAGNETIC LOCATION SENSOR AND ULTRASOUND ARRAY ON PRINTED-CIRCUIT-BOARD (PCB) OF CATHETER AND CALIBRATION THEREOF

CROSS-REFERENCE TO RELATED APPLICATION

This application is a divisional of U.S. patent application Ser. No. 17/483,065, filed on Sep. 23, 2021, the contents of which are incorporated by reference as if set forth in its entirety herein.

FIELD OF THE INVENTION

The present invention relates generally to medical probes, and particularly to intracardiac probes comprising ultrasound arrays and location sensors.

BACKGROUND OF THE INVENTION

Techniques to realize location sensors on catheters have been previously proposed in the patent literature. For example, U.S. Patent Application Publication 2018/0228392 describes a position sensor that includes a flexible substrate formed into a three-dimensional (3D) shape. At least first and second field-sensing coils are formed in first and second respective layers of the flexible substrate, such that in the 3D shape the first and second field-sensing coils have first and second respective axes that are not parallel to one another.

Invasive ultrasound imaging of cardiac cavities is a known diagnostic technique, which requires calibration to produce reliable images. For example, U.S. Pat. No. 7,996,057 describes an apparatus that has a rigid mechanical framework, for calibration of a probe that includes a magnetic position sensor and an acoustic imaging device. One or more field generators, fixed to the framework, generate a magnetic field of known spatial characteristics. An acoustic target assembly includes a phantom coupled to a motion mechanism, which is arranged to move the phantom in a known orbit relative to the framework. A jig, fixed to the framework, holds the probe within the magnetic field of the one or more field generators, in an orientation suitable for the imaging device to image the phantom. A processor processes position and image signals from the probe in order to calibrate coordinates of the imaging device relative to the position sensor.

As another example, U.S. Pat. No. 9,468,422 describes a sensor coupled to an ultrasound probe, which provides position information related to an ultrasound imaging position in an object. A processor performs first registration between the medical image and the ultrasound image, which provides a relationship between a coordinate system of the medical image and a coordinate system of the ultrasound image. That way, the processor obtains first registration information based on the first registration. The processor performs second registration between the sensor and the medical image based on the position information and the first registration information, and obtains second registration information based on the second registration.

SUMMARY OF THE INVENTION

An embodiment of the present invention that is described hereinafter provides a medical probe including a shaft and a distal-end assembly. The shaft is configured for insertion into an organ of a body. The distal-end assembly is fitted at a distal end of the shaft. The distal-end assembly includes (a) a substrate, (b) a two-dimensional (2D) ultrasound transducer array located on the substrate, and (c) a sensor which is also located on the substrate. The sensor is configured to output signals indicative of a position and an orientation of the 2D ultrasound transducer array inside the organ.

In some embodiments, the substrate is flexible and has at least a flat portion and a curved portion, and the sensor includes at least a first sensing element located on the flat portion and a second sensing element located on the curved portion.

In other embodiments, the first sensing element, which is located on the curved portion of the flexible substrate, has an axis of symmetry that is parallel with a longitudinal direction of the distal-end assembly.

There is additionally provided, in accordance with another embodiment of the present invention, an apparatus for calibration. The apparatus includes a mount, one or more acoustic targets, multiple magnetic-field generators, and a processor. The mount is adapted to hold a medical probe including (i) an array of ultrasound transducers that emit an ultrasonic beam and receive reflected ultrasound waves in response to the ultrasound beam, and (ii) a magnetic position sensor. The one or more acoustic targets are mounted within a field-of-view of the ultrasonic beam. The multiple magnetic-field generators are configured to generate a magnetic field in a vicinity of the magnetic position sensor. The processor is configured to (a) receive from the ultrasound transducers first signals indicative of the reflected ultrasound waves, (b) receive from the position sensor second signals indicative of a position and an orientation of the position sensor, and (c) determine, based on the first signals and the second signals, a registration between the position sensor and the array of ultrasound transducers.

In some embodiments, the processor is configured to (i) generate, from the first signals, multiple ultrasound images corresponding to multiple respective positions and orientations of the medical probe relative to the mount, (ii) identify, from among the multiple ultrasound images, an ultrasound image that matches a predefined reference image including the acoustic targets, and (iii) determine the registration based on the second signals, which were received from the position sensor at the position and orientation that yielded the ultrasound image that matches the predefined reference image.

In an embodiment, the acoustic targets are shaped as balls.

In another embodiment, the mount and the one or more acoustic targets are non-ferromagnetic.

In yet another embodiment, at least one of the acoustic targets includes a moving acoustic target.

There is further provided, in accordance with another embodiment of the present invention, a method for calibration, including holding with a mount a medical probe including (i) an array of ultrasound transducers that emit an ultrasonic beam and receive reflected ultrasound waves in response to the ultrasound beam, and (ii) a magnetic position sensor. One or more acoustic targets are mounted within a field-of-view of the ultrasonic beam. A magnetic field is generated in a vicinity of the magnetic position sensor. First signals are received from the ultrasound transducers, the first signals indicative of the reflected ultrasound waves. Second signals are received from the position sensor, the second signals indicative of a position and an orientation of the position sensor. Based on the first signals and the second signals, a registration is determined between the position sensor and the array of ultrasound transducers.

In some embodiments, determining includes generating, from the first signals, multiple ultrasound images corresponding to multiple respective positions and orientations of the medical probe relative to the mount. An ultrasound image is identified from among the multiple ultrasound images, that matches a predefined reference image including the acoustic targets. The registration is determined based on the second signals, which were received from the position sensor at the position and orientation that yielded the ultrasound image that matches the predefined reference image.

The present invention will be more fully understood from the following detailed description of the embodiments thereof, taken together with the drawings in which:

DETAILED DESCRIPTION OF EMBODIMENTS

Overview

Figure 1:
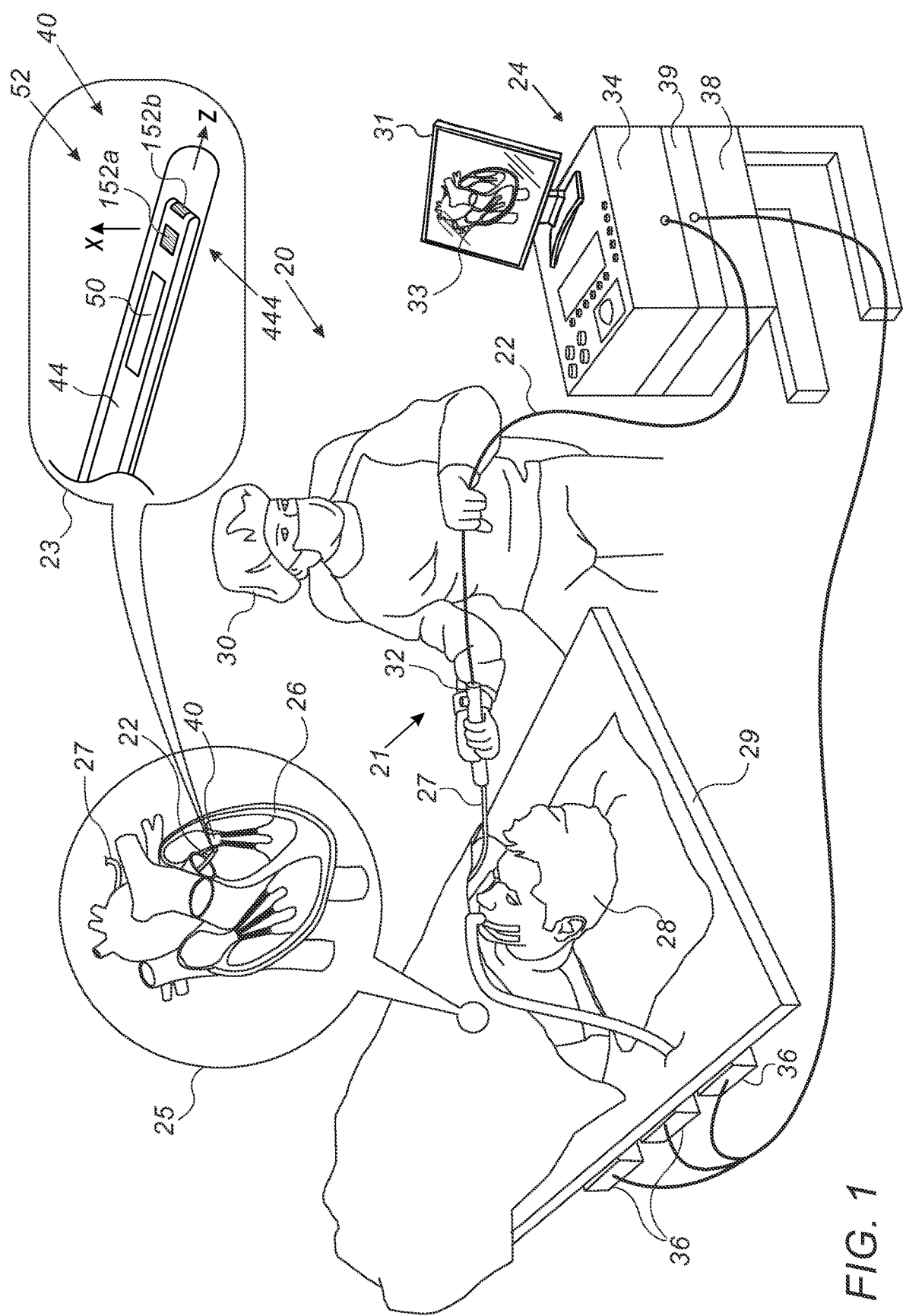
FIG. 1 is a schematic, pictorial illustration of a catheter-based system for ultrasound imaging and position tracking, in accordance with an embodiment of the present invention.

Embodiments of the present invention that are described hereinafter provide methods and systems for ultrasound imaging using an intra-body probe, such as a catheter, and for calibration of such probes. Some of the disclosed embodiments use a probe, such as a catheter, having a two-dimensional (2D) array of ultrasound transducers for producing three-dimensional (3D) or four-dimensional (4D) ultrasound images. In the present context, the term "3D ultrasound image" refers to an ultrasound image that represents a certain volume in three dimensions.

The term "4D ultrasound catheter" refers to a catheter incorporating a 2D array of ultrasound transducers. The term "4D ultrasound image" refers to a time series of 3D ultrasound images of a certain volume acquired by the 2D array. A 4D image can be regarded as a 3D movie, the fourth dimension being time. Another way of describing a 4D image (or rendering) is as a time-dependent 3D image (or rendering). Where used in the heart, a 4D ultrasound catheter may be referred to as "4D Intracardiac Echocardiography (ICE)" catheter.

In the embodiments disclosed herein, the catheter also comprises an integral location sensor having one or more sensing elements, such as a magnetic position sensor having one or more coils, that is pre-registered with the 2D array based on the known relative position and orientation on the catheter shaft between the location sensor and the 2D array. The 2D array produces a 3D sector-shaped ultrasound beam occupying a defined solid angle; (such a beam is referred to herein as a "wedge," as opposed to a 1D array "fan"). The 2D array is thus able to image a 2D section of an inner wall of an organ, such as of a cardiac chamber. Because of the integral location sensor, and its pre-registration with the 2D array, the spatial coordinates of every voxel in the imaged section are known.

In some embodiments of the present invention, the ultrasound transducer array is mounted on a substrate, such as a flexible printed circuit board (referred to as "flex PCB" or "flex circuit"), and the location sensor is also disposed on the same PCB. In disclosed embodiments the location sensor is a magnetic location sensor, such as a single-axis/dual-axis/triple-axis sensor (SAS/DAS/TAS).

In one embodiment, the location sensor is a DAS comprising two orthogonal coils, one of the coils being on the plane surface of the flex circuit, to define a roll angle of the distal-end assembly. The other coil is formed on a curved portion of the flex circuit, to define a longitudinal direction of the distal-end assembly. Therefore, the axis of symmetry of this coil defines a direction in space of the distal end assembly. In the case of a TAS, a third coil, having an axis of symmetry not parallel to either of the flex-disposed coils, may be a stand-alone unit disposed on the PCB.

In assembling such a catheter, the 2D array of ultrasound transducers and the magnetic location sensor should be registered with a common coordinate system, so that the signals provided by the sensor give a processor means to determine the location and/or direction and/or orientation of the array. A transfer function of the registration should be provided to the system operating the catheter.

Some embodiments of the invention provide a jig comprising a chamber into which the catheter can be placed and adjusted with six degrees of freedom. The jig comprises magnetic-field generators, similar to those of a location pad of a tracking system of the system operating the catheter. The jig is designed so that there is one point in the jig at which, if the ultrasound transducer array is centrally located and is oriented correctly, the 2D-array ultrasound image generated is unique. To this end, the jig further comprises "acoustic targets," defined hereinafter as physical objects that have known geometries and positions and reflect ultrasound waves well (i.e., appear in images as high contrast objects). In an embodiment, the acoustic targets are a set of different sized balls positioned so that if the array center is correctly placed at a point in space, $\vec{r}_0$, the balls image is unique, as described below. Although the jig is to register a 2D ultrasound array, it may also be used to register other types of ultrasound imaging devices, e.g., 1D arrays.

Once the catheter has been adjusted to give a predefined and identifiable unique ultrasound image, its location sensor readings are acquired. The location sensor readings are used to generate calibration data, typically a transfer function for the catheter. The function is stored on a non-volatile memory, e.g., an EEPROM that accompanies the catheter, or on a memory of the position tracking and ultrasound imaging system.

In practice, the 2D ultrasound array, and more generally any ultrasound imaging device in use in the catheter, and the magnetic sensor are calibrated in separate steps, within their own, distinct coordinate systems. To correlate coordinates (e.g., locations, directions, roll-angles) measured using both sensors, a registration of the coordinate systems of the ultrasound imaging device with that of the magnetic position sensor is performed in a single apparatus (i.e., in the jig).

In one embodiment, the use of acoustic targets enables automatic identification of the targets, automatic calibration, and subsequent automatic analysis of the ultrasound images from the imaging device using image processing techniques.

In some embodiments, the jig is made entirely of non-ferromagnetic materials, and therefore is suitable for use in conjunction with a magnetic calibration apparatus. In this manner calibrations and registration are made in a single apparatus, as described below. In some embodiments, a calibration process of the position sensor provides a transfer function comprising calibration factors for use in computing coordinates applicable to ultrasound images formed by the probe based on readings of the position sensor. In some embodiments, the calibration factors are also used for determining a physical displacement along a longitudinal axis of the probe, or along any other axis between the magnetic sensor and the acoustic imaging device.

System Description

FIG. 1 is a schematic, pictorial illustration of a catheter-based system 20 for ultrasound imaging and position tracking, in accordance with an embodiment of the present invention. A physician 30 (such as an interventional cardiologist) inserts catheter 21 through the vascular system of a patient 28 lying on a medical table 29. Catheter 21 comprises a shaft 22 and a distal-end assembly 40 fitted at a distal end of shaft 22. Assembly 40 comprises a dual-axis position sensor (DAS) 52 and an ultrasound 2D-array 50, shown in an inset 23. Physician 30 moves assembly 40 of catheter 21 in the vicinity of the target region in heart 26, as shown in an inset 25, by manipulating catheter 21 with a manipulator 32 near the proximal end of the catheter. The proximal end of catheter 21 is connected to interface circuitry 34 in a console 24 to convey and receive signals from DAS 52 and 2D-array 50.

A cardiac chamber or a portion of a chamber may be imaged when the physician causes the catheter shaft, onto which the 2D array is mounted, to translate, deflect, and/or rotate such that additional portions of the cardiac chamber come within the field of view of ultrasound wedge 250. Exemplary intravascular catheters and imaging assemblies that enable such deflection and rotation are described in detail in U.S. Pat. Nos. 9,980,786; 10,537,306; and U.S. Patent Publication No. 2020-0061340 A1, whose disclosures are all incorporated herein by reference.

As seen in inset 23, DAS 52 comprises coils 152a and 152b with approximately mutually orthogonal axes, x and z, respectively. To this end, DAS 52 is integrated on a flexible substrate 44 (e.g., a flexible printed-circuit board (PCB)) formed into a three-dimensional (3D) shape. In particular, coil 152b is disposed on a curved portion 444 of flexible substrate 44. Ultrasound array 50 is mounted on flex PCB 44, as well.

Using coils 152a and 152b processor 39 can determine a roll-angle and a direction of 2D array 50. To this end, console 24 further comprises a driver circuit 38, which drives magnetic field generators 36 placed at known positions external to patient 28, e.g., below the patient's torso. Physician 30 can view the position of assembly 40 in an image 33 of heart 26 on a user display 31.

The method of position sensing is implemented, for example, in the CARTO™ system, produced by Biosense Webster. and is described in detail in U.S. Pat. Nos. 5,391, 199, 6,690,963, 6,484,118, 6,239,724, 6,618,612 and 6,332, 089, in PCT Patent Publication WO 96/05768, and in U.S. Patent Application Publications 2002/0065455 A1, 2003/ 0120150 A1 and 2004/0068178 A1, whose disclosures are all incorporated herein by reference.

System 20 uses 2D-array 50 for imaging the heart in the vicinity of distal-end assembly 40. Ultrasound 2D array 50 is driven with suitable electrical signals by a signal generator (not shown) included in console 24. In response to these signals, 2D-array 50 emits ultrasound waves that irradiate an intracardiac volume surrounding distal end of assembly 40. 2D-array 50 receives the ultrasound wave reflected from sonically irradiated cardiac tissue and converts the reflected wave ("echo") to electrical signals.

An example of a suitable 2D array is described in D. Wildes et al., "4-D ICE: A 2-D Array Transducer with Integrated ASIC in a 10-Fr Catheter for Real-Time 3-D Intracardiac Echocardiography," in IEEE Transactions on Ultrasonics, Ferroelectrics, and Frequency Control, vol. 63, no. 12, pp. 2159-2173, December 2016, doi: 10.1109/ TUFFC.2016.2615602, which is incorporated herein by reference in its entirety.

2D-array 50 is a phased array comprising individual transducers (not shown) that generates a sector "wedge" beam to acquire a volumetric section of a cardiac chamber at each scanning step. Such a two-dimensional ultrasound phased array is described, for example, in U.S. patent application Ser. No. 17/357,231, filed Jun. 24, 2021, titled "Reconstructing a 4D Shell of a Volume of an Organ Using a 4D Ultrasound Catheter," which is assigned to the assignee of the present patent application and whose disclosure is incorporated herein by reference.

As shown in inset 23, DAS 52 and 2D-array 50 are located at certain respective distances one from the other due to physical constraints in the construction of assembly 40. The actual position of a wedge beam generated by 2D-array 50 is computed by calibrating, for example, a longitudinal displacement between DAS 52 and array 50. The actual roll-angle of the 2D-array 50 is also calibrated. The calibration may be realized as a transfer function for the catheter. The function can be stored in memory 37 of console 34 or, for example, on a non-volatile memory in the catheter handle.

Processor 39 is typically a general-purpose computer, with suitable front end and interface circuits for receiving signals from catheter 21 and for controlling the other components of system 20 described herein. Processor 39 may be programmed in software to carry out the functions that are used by the system, and the processor stores data for the software in a memory 37. The software may be downloaded to console 24 in electronic form, over a network, for example, or it may be provided on non-transitory tangible media, such as optical, magnetic or electronic memory media. Alternatively, some or all of the functions of processor may be carried out by dedicated or programmable digital hardware components.

Although FIG. 1 shows a particular system configuration, other system configurations may be used in alternative embodiments of the present invention. For example, catheter 21 may comprise any other suitable type of position sensor known in the art, such as other types of field-sensing devices, e.g., a Hall Effect sensor. Alternatively, DAS 52 may generate magnetic fields, which are detected by sensing antennas outside the body. The principles of the present invention are applicable to substantially any position-sensing technology that can be implemented in a medical probe. Assembly 40 may further include one or more mapping electrodes (not shown).

PCB-Based Magnetic Location Sensor and 2D Ultrasound Array for Catheter

Figure 2:
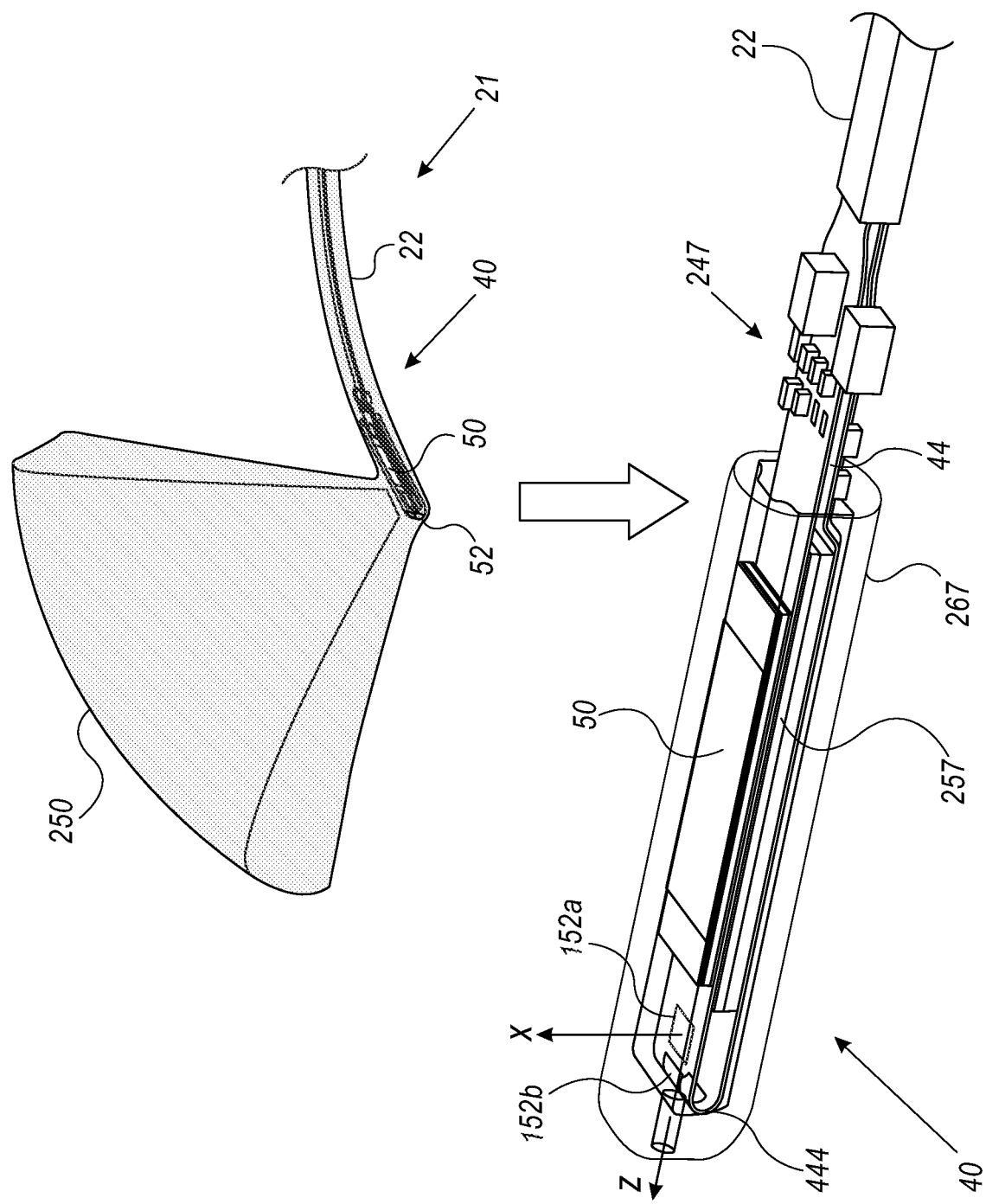
FIG. 2 is a schematic, perspective view of the distal-end assembly of the intracardiac ultrasound imaging catheter of FIG. 1, in accordance with an embodiment of the present invention.

FIG. 2 is a schematic, perspective view of distal-end assembly 40 of intracardiac ultrasound imaging catheter 21 of FIG. 1, in accordance with an embodiment of the present invention. Catheter 21 is shown at the top with a schematic wedge beam 250 that 2D-array 50 emits in response to driving signals applied to the transducers of array 50.

A schematic detailed structure of distal-end assembly 40, at the bottom of the figure, shows 2D-array 50 and coils 152a and 152b of DAS 52 of FIG. 1. 2D-array 50 is mechanically supported by a plate 257. A portion of flexible PCB 44 having both elements 52 and 50 is encapsulated with a suitable encapsulation 267. The flexible PCB is further disposed with electronic elements 247 that facilitate the operation of DAS 52 and ultrasound array 50, as well as, optionally, of other elements on the distal-end, such as electrodes and temperature sensors.

Finally, as seen, to have coils 152a and 152b with approximately mutually orthogonal axes, orientation axis x and longitudinal (direction) axis z, coil 152a is disposed on a flat portion of flexible substrate 44 while coil 152b is disposed on curved portion 444 of flexible substrate 44.

The sensors (e.g., coils) can be also attached to the transducer PCB rigid part as one unit comprising all sensors, or multiple units. In that regard, a sensor can be attached as any other electric component. A position sensor can be a single TAS sensor or multiple SAS sensors each orthogonal to each other.

Calibration of PCB-Based Magnetic Location Sensor and 2D Ultrasound Array of Catheter As indicated above, an embodiment of the disclosed invention provides an apparatus for calibration, such as apparatus 300 described below. The apparatus comprises (a) a mount, which is adapted to hold a medical probe comprising (i) an array of ultrasound transducers that emit an ultrasonic beam and receive reflected ultrasound waves in response to the ultrasound beam, and (ii) a magnetic position sensor, (b) one or more acoustic targets, which are mounted within a field-of-view of the ultrasonic beam, and (c) multiple magnetic-field generators, configured to generate a magnetic field in a vicinity of the magnetic position sensor, and (d) a processor, configured to:
  (i) receive from the ultrasound transducers first signals indicative of the reflected ultrasound waves;
  (ii) receive from the position sensor second signals indicative of a position and an orientation of the position sensor; and
  (ii) determine, based on the first signals and the second signals, a registration between the position sensor and the array of ultrasound transducers.

The processor may be further configured to:
  (i) generate, from the first signals, multiple ultrasound images corresponding to multiple respective positions and orientations of the medical probe relative to the mount;
  (ii) identify, from among the multiple ultrasound images, an ultrasound image that matches a predefined reference image comprising the acoustic targets; and
  (iii) determine the registration based on the second signals, which were received from the position sensor at the position and orientation that yielded the ultrasound image that matches the predefined reference image.

Figure 3:
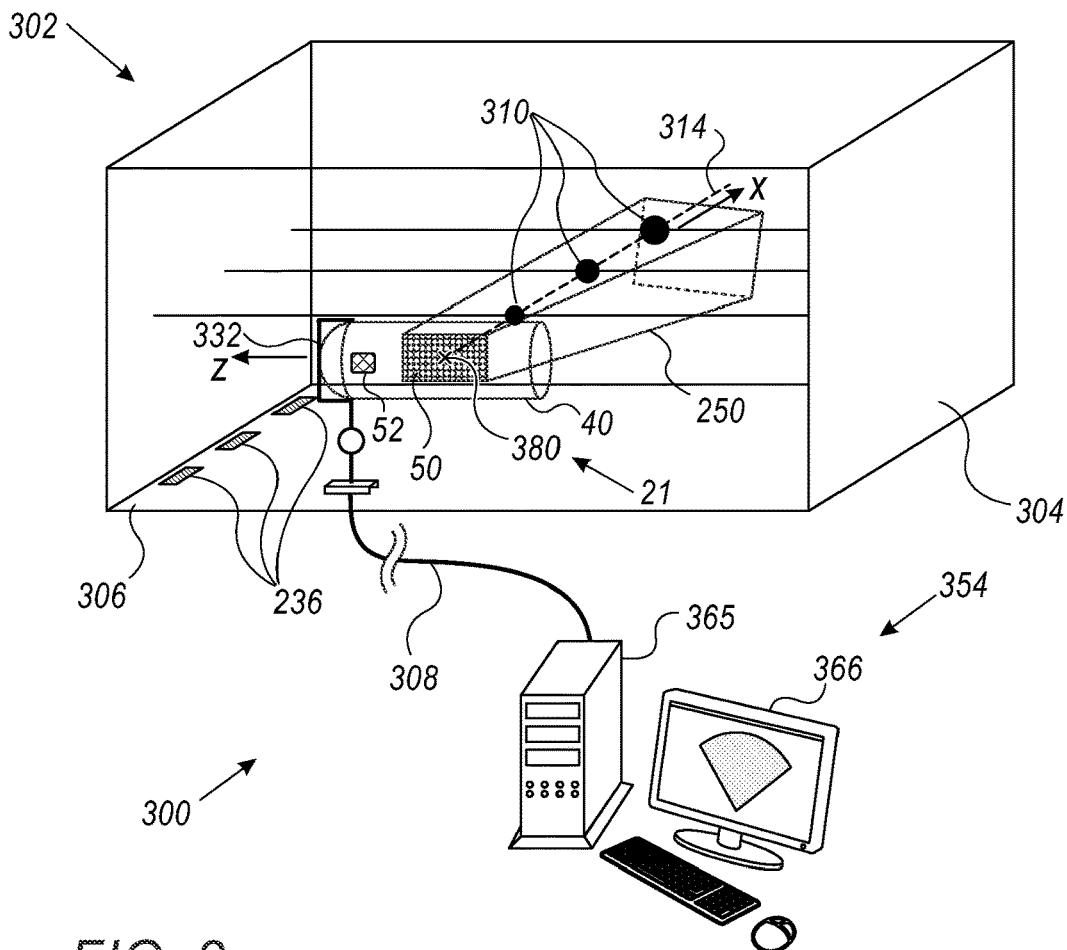
FIG. 3 is a schematic, pictorial illustration of an apparatus for calibration of the intracardiac ultrasonic imaging catheter of FIG. 1, in accordance with an embodiment of the present invention.

FIG. 3 is a schematic, pictorial illustration of an apparatus 300 for calibration of intracardiac ultrasonic imaging catheter 21 of FIG. 1, in accordance with an embodiment of the present invention. Apparatus 300 comprises a calibration jig 302 that can be coupled with catheter 21 requiring calibration, and a calibration console 354.

Catheter 21 is electrically connected to calibration console 354 (cable not shown) to convey position signals from DAS 52, and ultrasound signals from 2D array 50. Additional cabling exists, such as used for driving the various elements of distal-end assembly 40, and is omitted for clarity.

Jig 302 comprises a chamber 304 having a base 306, which serves as a rigid mechanical framework for a set of magnetic field generators 236 and acoustic targets 310. Magnetic field generators 236 are typically similar to magnetic field generators 36 of FIG. 1.

Jig 302 is connected to a calibration console 354 via a cable 308, which is used for conveying driving signals to generators 236. Based on direction and orientation signals that DAS 52 generates in response to magnetic fields emitted by generators 236, processor 365 determines the location and orientation of the DAS for each 2D ultrasound image captured by 2D-array 50.

Applying ultrasound calibration and magnetic calibrations in the same set-up enables processor 365 to perform highly accurate registration of the coordinate systems of each of the two modalities. This accuracy is manifested by finding, for example, exact displacements between the origins of the ultrasonic and magnetic coordinate systems. These origins are typically defined as the center 380 of the transducer 2D-array 50 and the centers of coils 152a and 152b.

In the present example, jig 302 is made entirely of non-ferromagnetic materials to enable its use in a magnetic calibration apparatus. Distal-end assembly 40 of catheter 21 is inserted into a suitable mount 332 of Jig 302 that includes one or more fixtures (with total of six degrees of freedom) to guide distal-end assembly 40 to a given position within chamber 304 of jig 302 and hold distal-end assembly 40.

As noted above, for performing the calibrations, calibration console 354 is used, which typically comprises a processor 365 with suitable signal processing and user interface circuits. Typically, console 354 enables a user to observe and regulate the functions of catheter 21 and displays on a monitor (display) 366 ultrasound images of acoustic targets 310 that are imaged using the catheter. The balls may be made of any suitable ultrasound-reflecting material that is not ferromagnetic.

As seen in FIG. 3, catheter 21 is aligned such that wedge beam 250 that 2D-array 50 emits covers acoustic target balls 310. When the catheter is well aligned, target balls 310 lie in a line 314 (i.e., aligned) parallel to x direction (the orientational axis), orthogonal to the z direction (the longitudinal axis of distal-end assembly 40) and are scanned orthogonally by wedge beam 250 from the aforementioned position $\vec{r}_0$ of the catheter that, for example, is where the center 380 of the transducer 2D-array 50 located at after catheter 21 alignment. In other words, when distal-end assembly 40 is well aligned relative to balls 310, balls 310 will overlap each other in an ultrasonic beam plane, to create a unique image where all balls are merged to appear in a resulting ultrasound image as a single dot.

The example illustration shown in FIG. 3 is chosen purely for the sake of conceptual clarity. The type and arrangement of acoustic targets may vary, including, for example, movable targets, in addition to static balls, so as to measure a temporal resolution of images generated by 2D-Array 50. Other mechanical designs of fixtures, actuators, and additional mechanical elements of phantom jig 302 and respective alignment techniques will occur to a person skilled in the art.

Figure 4:
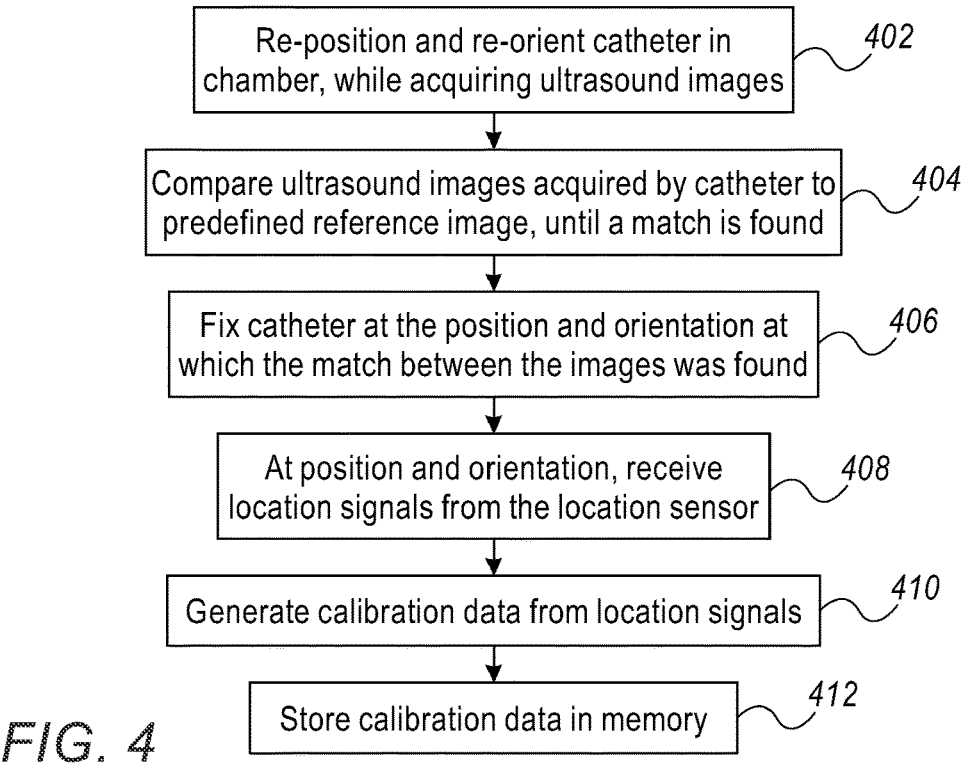
FIG. 4 is a flow chart that schematically illustrates a method for calibrating the intracardiac ultrasound imaging catheter of FIG. 1, in accordance with an embodiment of the present invention.

FIG. 4 is a flow chart that schematically illustrates a method for calibrating intracardiac ultrasound imaging catheter 21 of FIG. 1. The process begins by mechanically aligning distal end assembly 40 of catheter 21 in jig 302, at a catheter alignment step 402. In this step, a user re-positions and re-orients catheter in chamber, while acquiring ultrasound images using 2D-array 50.

Once the catheter has been properly positioned and oriented at step 402, processor 365 compares ultrasound images acquired by the catheter to a predefined reference image of ultrasound targets 310, until a match (e.g., overlap of targets in image) is found, at an ultrasound imaging & matching step 404.

To this end, acoustic targets 310 are arranged to intersect the plane of the ultrasonic beam one the catheter is at the given position and orientation angle (in other words, "properly positioned"). To this end, the acoustic targets (e.g., balls) are aligned on a line 314 that is parallel to orientation axis x of the distal-end assembly, when the catheter is well aligned mechanically.

At a catheter fixing step 406, the user fixes the catheter inside chamber 304 at the position and orientation at which the match between the images was found.

At this position and orientation, processor 365 receives location signals from the location sensor in response to the magnetic fields generated by field-generators 236, at location signals receiving step 408.

The use of acoustic targets 310 enables automatic identification of the targets using image processing techniques, followed by automatic calibration (e.g., coordinate registration between ultrasound array and sensor) based on automatic analysis of the ultrasound images from 2D-array 50.

Once the catheter generates ultrasound images that match the unique reference image, it can be assumed that the location and orientation of the sensor will give the necessary calibration data.

Thus, in a next calibration step 410, processor 365 generates calibration data from the location signals. The calibration data may be in a form of a registration matrix of ultrasound position and roll-angle with the coordinate system of the position tracking system that operates the location sensor. For example, the calibration data provides correction of (a) displacements between ultrasound 2D-array 50 and coils 152*a* and 152*b*, and (b) an angular displacement between orientation axis x of ultrasound 2D-array 50 (e.g., a normal to a 2D plane of ultrasound array 50) and the axis of symmetry of coil 152*a*. Finally, at a calibration data storage step 412, processor 365 stores calibration data in memory (e.g., EEPROM that will subsequently be mounted in catheter handle)

The example flow chart shown in FIG. 4 is chosen purely for the sake of conceptual clarity. In alternative embodiments, other ultrasound probes, for example one having a one-dimensional ultrasound array, may be calibrated by the same method. As another example a TAS is calibrated.

Although the embodiments described above make reference specifically to catheter 21, the principles of the present invention are equally applicable to other types of ultrasound probes, including both invasive probes and probes used outside the body.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus for calibration, comprising:
   a mount comprising a flexible printed circuit board (PCB), wherein the flexible PCB comprises a curved portion and a flat portion, and wherein the flexible PCB is adapted to hold a medical probe comprising (i) an array of ultrasound transducers that emit an ultrasonic beam and receive reflected ultrasound waves in response to the ultrasound beam, and (ii) a magnetic position sensor;
   one or more acoustic targets, which are mounted within a field-of-view of the ultrasonic beam;
   multiple magnetic-field generators, configured to generate a magnetic field in a vicinity of the magnetic position sensor; and
   a processor, configured to:
      receive, from the ultrasound transducers, first signals indicative of reflected ultrasound waves;
      receive, from the position sensor, second signals indicative of a position and an orientation of the magnetic position sensor; and
      determine, based on the first signals and the second signals, a registration between the magnetic position sensor and the array of ultrasound transducers.

2. The apparatus according to claim 1, wherein the processor is configured to:
   generate, from the first signals, multiple ultrasound images corresponding to multiple respective positions and orientations of the medical probe relative to the mount;
   identify, from among the multiple ultrasound images, an ultrasound image that matches a predefined reference image comprising the one or more acoustic targets; and
   determine the registration based on the second signals, which were received from the position sensor at the position and orientation that yielded the ultrasound image that matches the predefined reference image.

3. The apparatus according to claim 1, wherein the one or more acoustic targets are shaped as balls.

4. The apparatus according to claim 1, wherein the mount and the one or more acoustic targets are non-ferromagnetic.

5. The apparatus according to claim 1, wherein at least one of the one or more acoustic targets comprises a moving acoustic target.

6. The apparatus according to claim 1, wherein the magnetic position sensor comprises a first coil and a second coil, and wherein the curved portion comprises the first coil.

7. The apparatus according to claim 6, wherein the flat portion comprises the second coil.

8. The apparatus according to claim 7, wherein the first coil and the second coil comprise approximately mutually orthogonal axes.

9. The apparatus according to claim 8, wherein the magnetic position sensor comprises a third coil, and wherein the third coil is disposed on the flexible PCB with an axis of symmetry not parallel to either of the first coil or the second coil.

10. Method for calibration, method comprising:

holding, with a mount comprising a flexible printed circuit board (PCB), wherein the flexible PCB comprises a curved portion and a flat portion, a medical probe comprising (i) an array of ultrasound transducers that emit an ultrasonic beam and receive reflected ultrasound waves in response to the ultrasound beam, and (ii) a magnetic position sensor;

mounting within a field-of-view of the ultrasonic beam one or more acoustic targets;

generating, via multiple magnetic-field generators, a magnetic field in a vicinity of the magnetic position sensor;

receiving, from the ultrasound transducers, first signals indicative of the reflected ultrasound waves;

receiving, from the position sensor, second signals indicative of a position and an orientation of the position sensor; and determining, based on the first signals and the second signals, a registration between the position sensor and the array of ultrasound transducers.

11. The method according to claim 10, wherein determining the registration comprises:

generating, from the first signals, multiple ultrasound images corresponding to multiple respective positions and orientations of the medical probe relative to the mount;

identifying, from among the multiple ultrasound images, an ultrasound image that matches a predefined reference image comprising the acoustic targets; and determining the registration based on the second signals, which were received from the position sensor at the position and orientation that yielded the ultrasound image that matches the predefined reference image.

12. The method according to claim 10, wherein the acoustic targets are shaped as balls.

13. The method according to claim 10, wherein the mount and the one or more ultrasonic targets are entirely non-ferromagnetic.

14. The method according to claim 10, wherein mounting the acoustic targets comprises mounting at least one moving acoustic target.

* * * * *